United States Patent [19]
Rodgers

[11] Patent Number: 5,403,263
[45] Date of Patent: Apr. 4, 1995

[54] METHOD OF REDUCING THE RECOVERY TIME AND STRESS ASSOCIATED WITH SURGERY

[75] Inventor: Linda Rodgers, Katonah, N.Y.

[73] Assignee: P.I.P. Surgical Audiotape Series, Inc., Katonah, N.Y.

[21] Appl. No.: 886,995

[22] Filed: May 21, 1992

[51] Int. Cl.$^6$ .......................................... A61M 21/00
[52] U.S. Cl. ...................... 600/28; 128/898
[58] Field of Search ...................... 600/26–28; 128/897–898

[56] References Cited

U.S. PATENT DOCUMENTS 3,140,709  7/1964  Weisz ..................................... 600/28
3,235,316  9/1965  Hechler ................................. 600/28

FOREIGN PATENT DOCUMENTS 3628420  2/1988  Germany ............................... 600/28

OTHER PUBLICATIONS

Atterbury et al, Auditory Distraction Analgesia, Oct. 1964.
Ejektor, Relaxation Generator, Nov. 1977.
Buchsbaum, Electronic Anesthesia, Sep. 1963.
Brown, et al., "Silent Music Soothes the Surgical Patient", *The Modern Hospital* 72(4): 51–53 (1949).
Light, et al., "Music in Surgery", *Music Therapy* pp. 171–175 (1953).
Wolfe, et al., "Control of Post-Operative Pain By Suggestion Under General Anesthesia", *Am. J. Clin. Hyp.* 3: 109–112 (1960).
Pearson, R. E. P., "Response to Suggestions Given Under General Anesthesia", *Am. J. Clin. Hyp.* pp. 106–114 (1961).
Terrell, et al., "Study of Recall During Anesthesia", *Anesthesia and Analgesia . . . Current Researches* 48(1): 86–90 (1969).
Field, P. B., "Effects of Tape-Recorded Hypnotic Preparation For Surgery", *Int. J. Clin. Exp. Hyp.* XXII:(1) 54–61 (1974).
Marshall, M. A., "Behaviour Modification: Three Techniques for Decreasing the Stress of Hospitalization and Surgery", *CMA Journal* 119: 45–47 (1978).
Verheeck, et al., "Music While Your Wait-Patient Acceptance of Music in the Preanesthetic Period", *Acta Anaesthesiologica Belgica* 1: 61–65 (1980).
Gulledge, et al., "Use of Stereo Headphones for Patient Relaxation During Cataract Surgery Under Local Anesthesia", *Ophthalmic Surg.* 12:(4) 289–290 (1981).
George, et al., "The Effects of Psychological Factors on Recovery From Surgery", *JADA* 105: 251–258 (1982).
Mumford, et al., "The Effects of Psychological Intervention on Recovery From Surgery and Heart Attacks: An Analysis of the Literature", *AJPH* 72(2): 141–151 (1982).
Halpern, et al., "Sound Medicine", *Sound Health, The Music and Sounds That Make Us Whole*, 1st Ed. pp. 56–65 (1985).

(List continued on next page.)

Primary Examiner—Lee S. Cohen
Assistant Examiner—John P. Lacyk
Attorney, Agent, or Firm—Pennie & Edmonds

[57] ABSTRACT

A method of reducing anxiety and the recovery time of a patient during the preoperative, intraoperative and postoperative phases of surgery. The method includes the steps of providing music in each phase of the surgery in combination with voice-over information relating to each phase of the surgery that the patient experiences at the time, with information, reassurance and suggestions to help the patient relax and feel comfortable during the three phases of surgery.

27 Claims, No Drawings

OTHER PUBLICATIONS

Bennett, H., "Behavioral Anesthesia", *Advances, Institute for the Advancement of Health* 2:(4) 11–21 (1985).

Egbert, et al., "Reduction of Postoperative Pain by Encouragement and Instruction of Patients", *Advances* 2:(4) 53–56 (1985).

Moss, et al., "Hypnosis and the Surgical Patient, Effects of Positive Suggestion", *AORN Journal* 42:(3) 389–400 (1985).

Bonke, et al., "Clinical Study of So-Called Unconscious Perception During General Anaesthesia", *British J. Anaesth.* 58: 957–964 (1986).

Binnings, E., "The Effect of an Auditory Distraction on Anxiety in Ambulatory Surgical Patients Experiencing Regional Anesthesia", *J. Amer. Assoc. Nurse Anesth.* 55:(4) 333–335 (1987).

Woo, et al., "The Lack of Response to Suggestion Under Controlled Surgical Anesthesia", *Acta Anesthesiol Scand.* (31): 567–571 (1987).

Evans, et al., "Improved Recovery and Reduced Postoperative Stay After Therapeutic Suggestions During General Anaesthesia", *Lancet* ii: 491–493 (1988).

Moss, V. A., "Music and the Surgical Patient, The Effect of Music on Anxiety", *AORN Journal* 48(1): 64–69 (1988).

Goleman, D., "Doctors Find that Surgical Patients May Still Hear Despite Anesthesia", *N.Y. Times* Oct. 26, 1989 at B12.

Halpern, S., "A New Age of Music in Medicine", *Rehabilitation, Music and Human Well-Being*, Lee H. M. Mathew, Ed., MMB Music Inc., St. Louis pp. 76–81 (1989).

Harvey, A. W., "On Developing a Program in Music Medicine: A Neurophysiological Basis for Music as Therapy", *Music Medicine*, Spintge and Droh Ed. pp. 71–79 (1989).

Spintge, R., "The Anxiolytic Effects of Music", *Rehabilitation, Music and Human Well-Being*, Lee H. M. Matthew Ed., MMB Music Inc., St. Louis pp. 82–97 (1989).

Munch, et al., "Do Intraoperative Suggestions Prevent Nausea and Vomiting in Thyroidectomy-Patients? An Experimental Study", *Memory and Awareness in Anaesthesia* pp. 195–188 (1990).

Furlong, M., "Positive Suggestions Presented During Anaesthesia", *Memory and Awareness in Anaesthesia* pp. 170–175 (1990).

Jelicic, et al. "Indirect Memory for Words Presented During Anaesthesia", *The Lancet* 336: p. 249 (1990).

McLintock, et al., "Postoperative Analgesic Requirements in Patents Exposed to Positive Intraoperative Suggestions", *British Med. J.* 301: 788–790 (1990).

"Comforting Words", *Harvard Health Letter* 16:(3) (1991).

Bethune, et al., "Intraoperative Therapeutic Suggestions Improve Recovery Following Cardiac Surgery", *Memory and Awarness in Anesthesia* pp. 154–161 (1993) and abstract from *Emory University School of Medicine, Department of Anesthesiology and Emory University Department of Psychology*–Second International Symposium on Memory and Awareness in Anesthesia, Apr. 23–25, 1992.

Enqvist, et al., "Preoperative and Perioperative Therapeutic Suggestions–Somatic Responses During Surgery in General Anaesthesia", *Emory University School of Medicine, Department of Anesthesiology and Emory University Department of Psychology*–Second International Symposium on Memory and Awareness in Anesthesia, Apr. 23–25, 1992.

Furlong, et al., "Therapeutic Suggestions During General Anesthesia", *Memory and Awareness in Anesthesia* pp. 166–175 (1993) and abstract from *Emory University School of Medicine, Department of Anesthesiology and Emory University Department of Psychology*–Second International Symposium on Memory and Awareness in Anesthesia, Apr. 23–25, 1992.

Korunka, et al., "Effects of Positive Suggestions and Music Presented During Anesthesia", *Memory and Awareness in Anesthesia*, pp. 196–204 (1993) and abstract from Emory University School of Medicine, Department of Anesthesiology and Emory University Department of Psychology –Second International Symposium on Memory and Awareness in Anesthesia, Apr. 23—25, 1992.

(List continued on next page.)

OTHER PUBLICATIONS

Heitz, et al., "Effect of Music Therapy in the Postanesthesia Care Unit: A Nursing Intervention", *J. Post Anesth. Nursing* 7:(1) 22-31 (1992).

Aldridge, D., "Music Therapy Research 1: A Review of the Medical Research Literature Within a General Context of Music Therapy Research", *The Arts in Psychotherapy* (20): 11-35 (1993).

Pelletier, A. "Three Uses of Guided Imagery in Hypnosis", *The American Journal of Clinical Hypnosis* 22:(1) 32-36 (1979).

Ornstein, et al., "Coming to Our Senses", *Advances, Institute For The Advancement of Health* 6:(3) 49-56 (1989).

Miller, et al., "Letting Go Of Stress", Sound Rx; San Rafael, Calif., 1980.

Miller, E., "Successful Surgery And Recovery: Conditioning Mind And Body", Stanford, Calif., vol. 1 and 2, 1980.

"Musical Massage vol. 1", The Relaxation Company, Inc.; Manhasset, N.Y. 1981.

Halpern, S., "Effortless Relaxation", Sound Rx; San Anselmo, Calif. 1984.

Rossman, M., "Healing Yourself: Basic Relaxation Skills And Going Deeper Within", Insight Publishing; Mill Valley, Calif., 1987.

Therapeutic Suggestions in Hysterectomy, 1988.

Monroe Institute, Emergency Series, Interstate Industries, Inc.; Nellysford, Va., 22958, 1989.

Furlong, M., "Positive Suggestions Under Anesthesia", N.Y. 1990.

METHOD OF REDUCING THE RECOVERY TIME AND STRESS ASSOCIATED WITH SURGERY

COPYRIGHT NOTICE

A portion of the disclosure of this patent document contains material which is subject to copyright protection. The copyright owner has no objection to the facsimile reproduction by any one of the patent disclosure, as it appears in the Patent and Trademark Office patent files or records, but otherwise reserves all copyright rights whatsoever.

BACKGROUND OF THE INVENTION

Surgery is generally considered to involve three separate periods, the preoperative period, the intraoperative period and the postoperative period. The preoperative period covers a short period of time, anywhere from about 30 minutes to an hour or more, immediately preceding the intraoperative period.

In the intraoperative period, the surgical procedure or operation is performed with the time involved being anywhere from less than 30 minutes to a number of hours. During some surgical procedures, the patient may be placed under general anesthesia and completely unconscious. During other types of surgical procedures, the patient may be only lightly sedated or receive local or regional anesthesia.

The third postoperative period of surgery is the time immediately following the surgical procedure when the patient is moved to a recovery room or intensive care unit generally for an hour or more. The patient remains here until the effects of the anesthesia or sedation are dissipated and his or her condition stabilizes.

Together, these periods beginning with the preoperative period, continuing into the intraoperative period and concluding at the end of the postoperative period are referred to as the perioperative period.

Doctors and others involved with surgical patients have for some time recognized that the mental and emotional condition of a surgical patient can significantly affect the nature and time of recovery postoperatively. The literature demonstrates the positive effects of good psychological preparation prior to surgery.

Also, applicant is aware of the availability through commercial sale of two tapes for use by patients outside the hospital environment before surgery to aid the patient through the upcoming hospital stay. Such tapes are not prescribed by the medical staff performing the surgery. They include, as background, classical music played on a flute and a stringed instrument, together with voice-over suggestions and instructions urging the patient to relax and explaining in general terms the forthcoming surgical procedure. If the listener is familiar with the music, the effect could be either pleasing or not, depending upon the listener's past association with it. Similar tapes are available for sale to the patient in the weeks following surgery. Again, these tapes include similar music and voice instruction suggesting how to relax and thereby shorten the recovery time.

The literature also shows that during the actual surgical procedure, a patient under general anesthesia has the ability to hear and that the unconscious mind registers meaningful sounds, silence, and operating room conversations. There have only been a few studies conducted which document the effects of voice suggestions by a surgeon and anesthesiologist to patients during surgery.

One such study is discussed in an article published in The Lancet, Aug. 27, 1988, pages 491-493, entitled Improved Recovery and Reduced Postoperative Stay After Therapeutic Suggestions During General Anesthesia. The authors of the Lancet article, Carlton Evans and P. H. Richardson, describe a study they made of the use of tape recorded messages given to a group of patients only during the intraoperative period of surgery. The tape message was played to the patient during surgery and while under general anesthesia. A conventional auto-reverse tape player was used, with headphones making the operating theater sounds inaudible to the patient.

The beginning of the tape used in the Evans/Richardson study played music composed by Pachobel for the purpose of assuring that the tape was properly functioning before the message started. Being familiar music, the effect could be either pleasing or not, depending upon the patient's past association with it. It was not played for therapeutic purposes. The music was followed by three voice sections. The first section casually offered information about the surgery and described the normal postoperative procedure the patient would encounter and gave advice as to how to cope with this phase of the surgery by relaxing. As quoted in The Lancet, the transcript of the study reflects that the tape in this section stated, among other things, the following: "This is not a major operation . . . " Such a statement to a patient would not be permitted in this country because of its lack of universality, i.e., the variable kinds of surgery, health of patients, diagnoses and outcomes make one such general statement inappropriate and inaccurate. An operation may be major to some patients and minor to others. The transcript also reflects a statement in the tape to the effect that the surgery will "make you completely well again." Again, such a statement would not be permitted in this country, because no surgical procedure is uniformly so successful. This was followed by a second voice section containing therapeutic directives such as "you will feel fine", "you will not have any pain", and "your operation is a complete success." Finally, the tape concluded with suggestions to the patient by a member of the operating room staff to the effect that the operation is going well and that the patient is doing fine. Tapes of the nature used in the Evans/Richardson study would not be permitted in hospitals today in the United States, because one would not be permitted to offer to patients general comments, which will not be true for each and every such patient.

The results of the Evans/Richardson study were that patients using the tape recorded message spent significantly less time in the hospital after surgery than those who listened to a blank tape.

The literature further documents the value of music to sedate a person and the specific ways in which music, without extremes in rhythm, melody or dynamics and without familiarity or memory association, works to calm the listener. Such music is referred to as "anxiolytic" in that its purpose is to reduce anxiety. It differs from usual music which creates tension and then resolves such tension. Also, others well known in the mind/body field (i.e. experts in relaxation response, meditation, guided imagery, psychoneuroimmunology) have devised progressive relaxation and guided imagery techniques and other aids to help patients identify physical tension and learn how to relax. Guided imagery involves, for example, suggesting a safe or comfortable place such as a beach or other activity or locale familiar to the listener where the person can relax, such as a walk in the woods or a meadow, or resting in a room of your own with your own personal images and memory.

None of the prior art discloses the use of music, and particularly anxiolytic music, with voice-over information and suggestions for use by the patient through the perioperative period, that is, beginning with the preoperative period, continuing into the intraoperative period and concluding at the end of the postoperative period. Moreover, the prior art fails to disclose a voice delivery which is soft and slow with pauses to allow the patient to assimilate and follow what he is hearing. This is important in that patients under sedation or anesthesia, who may also feel anxious and fearful, tend to have difficulty understanding, assimilating, following or recalling the spoken word.

SUMMARY OF THE PRESENT INVENTION

In accordance with the teachings of the present invention, music and/or voice instructions and suggestions are given to a surgical patient to promote relaxation by showing the patient how to relax with the goal of reducing tension, anxiety, stress and discomfort which most patients experience during the perioperative period. For a surgical procedure in which the patient will undergo general anesthesia, the preferred system of the present invention includes the playing of three separate combinations of music and voice-over instructions and suggestions to the surgical patient, one for each of the three periods of surgery. For a surgical procedure in which the patient will only be sedated or receive regional or local anesthesia, the system of the present invention includes two separate combinations of music and voice-over, one for the preoperative period and one for both the intraoperative and postoperative periods.

Each combination includes voice-over information particularly directed to the period of surgery which the patient is experiencing at the time. In addition to this information, repetitious voice suggestions are made to the patient to relax. The suggestions provide reassurance in order to reduce the tension, anxiety, stress and discomfort that most patients usually experience with surgery.

The system of the present invention includes utilization of an audio cassette recorder playback machine to play the music and voice-over. This recorder has a mechanical device that enables the tape player to reverse the tape automatically and play the other side in order to give the patient continuous music and voice-over instructions and suggestions for the length of each perioperative period. The automatic reverse allows the patient to continue listening for as long as the preoperative, intraoperative or postoperative period continues, as the case may be. This is necessary because there are frequently delays during the perioperative period and each type of surgery, of course, is for a different length of time. Thus, the tapes have been designed to account for these variations in time periods. Continuous playing blocks intrusive anxiety-provoking hospital sounds.

The music of the system is anxiolytic and includes an opening theme, a middle section and closing theme, with the opening and closing themes being the same for each period of the surgery. The opening and closing music themes are the same for all tapes as are the middle sections. All the music sets forth a pattern of sounds which give an impression of an enveloping, soothing and cohesive structure. The music, like the suggestions being given, is intended to relax the patient and to reduce the tension, anxiety, stress and discomfort associated with surgery.

DESCRIPTION OF THE PREFERRED EMBODIMENTS

In the presently preferred embodiment of the invention, a combination of music and voice-over is provided and the following description will be directed to this embodiment. It is to be understood, however, that the music, anxiolytic, or the voice as described below can be used alone, to some advantage.

In the presently preferred embodiment of the invention as used for a patient undergoing general anesthesia, the music and voice-over combinations are provided in three separate tape cassettes, one for the preoperative period of surgery, one for the intraoperative period and one for the postoperative period. These tape cassettes are adapted to be used with a portable audio-reverse tape cassette player such as commercially available. Earphones are provided for the patient so as to block out extraneous hospital noises, particularly those in the operating theater and in the recovery room. These noises can be intrusive, startling, unpleasant and jarring to the patient. As used herein, the term "recovery room" includes the hospital "intensive care unit" where the most critical patients are often brought after the surgical procedure. Also, the term "surgical procedure" includes any invasive procedure, whether diagnostic or involving an actual operation.

The first, preoperative tape is especially made for patients to hear before they undergo the surgical procedure. This period of time is frequently particularly difficult for many patients who feel vulnerable given the uncertainty and normal anxiety with respect to the unknown surgical outcome. The preoperative tape is made in order to help the patient feel as comfortable as possible while the patient waits for the upcoming surgical procedure. This tape contains information about the preoperative time and also introduces the patient to the upcoming intraoperative and postoperative tapes. The tape acknowledges stress inherent in this preoperative waiting time; and by offering reassurance and suggestions to help the patient develop skills to relax, returns some degree of control to the patient who would otherwise remain alone and without the resources suggested by the voice over of the tape. Music is played throughout the duration of the recording.

It is preferable to listen to the preoperative tape approximately 30–45 minutes before the surgical procedure. However, the tape may also be listened to substantially prior to entry into the hospital, as for example, the night before. It can also be listened to several days or longer before hospitalization and surgery.

The music in the preoperative tape
- is known as anxiolytic in that it is composed to reduce anxiety and to facilitate relaxation;
- is composed without recognizable melody, familiar rhythm or harmony that can be anticipated, and it uses major rather than minor keys—the former generally accepted as peaceful and pleasing, the latter as somber and soulful;
- has been composed to allow each patient to respond according to the patient's personalized biorhythmic system, rather than according to familiar and anticipated harmony, melody and rhythm;

is composed to blend with the voice-over information and suggestions given to the patient; and is composed with an opening theme, middle section and a closing theme, the opening and closing themes being the same, and the two themes and middle section being joined without any discernable change in the music so as to provide a continual flow.

A representative preoperative tape of the present invention, © 1991 P.I.P. Surgical Audiotape Series, Inc., contains a voice-over which is divided into fifteen segments as set out below.

I. The tape that you are listening to was made especially for patients to hear before they have surgery. This is a particularly difficult time for everyone . . . this waiting time when it is often what we don't know that makes us feel even more scared. And so this tape was made in order to help you feel as comfortable as you can while you wait. We know that the more relaxed and comfortable you are, the more easily you will manage your surgery . . . and the more rapidly you will recover.

II. I am going to begin by giving you some information that will be useful to have before your surgery starts . . . and especially helpful to know about after your surgery is finished, and you begin your recovery.

III. For now, all you have to do is listen to the tape. The tape will play and repeat, and you may hear it over and over, right up until the time your surgery begins. As a matter of fact, I want you to listen as often as you can, because the more familiar you are with the information and suggestions, the easier you will find it to manage your surgery and recovery. Our goal is to help you make your surgery as comfortable as possible. And our goal is also to help you take charge of yourself and what happens to you—and to help you recover and return home as soon as possible.

IV. And now, I want you to begin to notice the music that has been playing in the background while I have been talking to you. It is music that was written especially for this tape . . . to help you relax. And so the music will continue to play throughout the tape. All you need to do is listen . . . and know that the music is there to help you feel more comfortable and relaxed. From time to time, while you hear the music playing, I will offer suggestions to help you relax even more.

V. Later, I will be talking to you again on another tape made especially for you to hear during your surgery. Although you will be "asleep" under a general anesthesia, there are many reasons to believe that you may continue to hear sounds and voices . . . and to understand what you hear. And so I will continue to give you information, and suggestions, and reassurance . . . and you will continue to hear the same music that you are hearing now on this tape.

VI. Still later, as you begin to wake up from the anesthesia, you will be able to hear a third tape. On this tape, I will repeat some of the suggestions that I have already made, but I will also add new information . . . the kind of information that other patients have found helpful and comforting to think about during their recovery from surgery.

VII. For now, the best thing that you can do is to listen to this tape . . . and so I want you to close your eyes, and close out the hospital . . . with your eyes closed, listen even more carefully to the messages on the tape . . . tune in to the music and the messages . . . and for now, tune out anything that bothers you.

VIII. To help you learn how to do this, I want you to start right now. Begin by closing your eye . . . letting your eyelids close slowly over your eyes, and now letting your eyes remain closed . . . your eyelids beginning to feel heavy over your eyes . . . And you have just taken the first step in taking charge of relaxing your body.

IX. Nobody knows exactly how it works, but we do know that when you simply think about wanting your body to relax, somehow you can make it happen . . . And so, with your eyes still closed, begin by thinking about your right hand. Make it into a fist . . . and now make it tight . . . squeeze your fist . . . tight. Even tighter. And now let it go . . . let your fingers go . . . let your fingers relax, and let your hand rest gently . . . Let your whole hand relax and rest. And now try the same thing with your left hand. Make a fist . . . tight. Tighter. Hold it tight. And now let your fingers rest, and let your whole hand relax. And now, if you feel like it, you can move on, and you can do the same thing with the rest of your body . . . Begin by thinking about a part of your body that feels really tense to you right now. Feel the tension . . . Think about the tension . . . and now tell that part of your body to relax, and let go, just as you told your fingers and your hand to relax, and let go, and rest.

MUSIC ALONE

X. As the music continues to play, remember that the music is there to help you feel even more relaxed. Now as the music plays, think about any other parts of your body that feel tense . . . Feel the tension there . . . and as the music plays, tell the muscles that feel tight and tense to relax . . . and imagine those muscles growing soft and heavy . . . and very, very relaxed.

MUSIC ALONE

And now let the softness spread to other parts of your body . . . Let it flow from the top of your head . . . and then . . . bit by bit, all the way down to your feet . . . and on down to the tips of your toes. Tell your whole body to rest and relax . . . And let your body grow even more deeply relaxed . . . let go the tension in your whole body . . . and feel so very, very relaxed . . . comfortable . . . calm . . . and very, very relaxed.

MUSIC ALONE

And now . . .

XI. . . . with your eyes still closed, and still feeling very, very relaxed, begin to listen to the music . . . music that has been written especially for you, to help you relax . . . music that has been playing while I have been talking to you . . . music that will continue to play softly. Rest now . . . and listen to the music . . .

MUSIC ALONE

. . . you don't have to think about anything else . . . just let the music bathe you in a warm bath of sound . . . let the music wash over your whole body . . . relaxing and soothing you . . . helping your whole body relax . . . allowing your muscles to relax, and let go their tension . . . letting your mind drift peacefully . . . letting your mind and your body rest and relax to the sound of the music . . .

MUSIC ALONE

And now . . .

XII. . . . with your eyes closed, feeling very, very relaxed listening to the music, and feeling completely relaxed and peaceful . . . I want you to take yourself off to another place . . . far, far away . . . a place that I will tell you about . . . a place where you can imagine yourself being . . . where you can take yourself now, and imagine that you are there . . .

XIII. Let it be an island, somewhere far, far away . . . with a beach . . . and miles and miles of clean, white, velvety soft sand . . . Take yourself there now, and feel the warm sand on the beach. Lie down on the sand and feel its warmth . . . feel the soft sand holding your body, and the sun warming your body as you rest on the beach . . . And now feel the breeze touching your skin, and hear the leaves of the palm trees brushing gently against each other . . . Hear the waves rolling up over the sand . . . each wave followed by another . . . rolling over and over, again and again . . . Smell the salt air . . . and now hear a seabird calling somewhere in the distance . . . And as you lie on the beach, relaxed and very, very comfortable, let this be your special place . . . Stay here as long as you like . . . resting and relaxing . . . knowing that when you leave, you may return any time that you wish . . . knowing that your special place will always be waiting for you . . . peaceful and safe . . . a place where you can always come and go whenever you wish . . . where you will always feel comfortable and calm . . . peaceful . . . and very safe . . . and very, very relaxed . . .

MUSIC ALONE

XIV. And now that you know how easy it is to go to your imaginary island, you may decide to travel to another place . . . Perhaps this one will be a place that you already know . . . a place that you remember well because you have always loved being there, and you know that you will enjoy being there again. Let this place be as peaceful as your island . . . Let it be a quiet, restful place where you will also feel comfortable and safe . . . Take yourself there now, and begin to imagine how it will look when you arrive . . . What will you see? Imagine yourself there, and find a spot that looks comfortable . . . See yourself sitting down . . . or perhaps you would rather lie down and stretch out to feel completely comfortable . . . When you have found your comfortable spot, look around and notice all the things that you see . . . Imagine seeing things that you know and love, and let yourself look closely at each object. Look at the shapes of the things around you, and notice whether they are big or small . . . Perhaps there is something that you want to hold or touch . . . it may be soft . . . perhaps it is heavy . . . notice its color . . . enjoy looking all around you . . . and if you feel like it, notice the sounds in this place . . . and the smells . . . the smell of something that you remember enjoying when you were here before . . . And now as you look around, take pleasure and comfort in being here . . . Feel yourself relaxing and enjoying your place . . . feel safe . . . and very peaceful . . . and very, very relaxed . . . And know that you may stay here as long as you wish . . . and that your place will always be here for you whenever you wish to return.

MUSIC ALONE

XV. Wherever it is that you imagine yourself to be, let it be a place that is always safe and comfortable . . . where you can listen to the music as you relax in your special place . . . and where you can drift with the music, floating back to sleep . . . relaxed and comfortable . . . very peaceful . . . and very, very relaxed.

MUSIC ALONE

And now . . .

The preoperative tape is recorded with the voice-over script initially playing through segments I through XV. The voice-over then goes back to pick up at segment XI and plays from segment XI to the end segment XV. This concludes side 1. Side 2 of the tape is the same as side 1; and the tape player automatically reverses to the second side of the tape.

The second intraoperative tape is, in some respects, similar to the preoperative tape. First of all, it includes the same type of anxiolytic music; the music is divided into an opening theme, a middle section and closing theme. The opening and closing themes of the intraoperative tape are the same as the opening and closing themes of the preoperative tape, and the middle section is also the same as the middle theme of the preoperative tape. This is for the purpose of orienting and giving the patient familiarity, comfort and continuity with the music of the preoperative tape. Such continuity is enhanced by the opening theme of the intraoperative tape matching the closing theme of the preoperative tape. The intraoperative tape is played to the patient during the entire surgical procedure. It is started before the general anesthesia has taken effect and the playing is continued while the patient is under general anesthesia.

While the music of the intraoperative tape plays continuously throughout the duration of the recording, the voice-over is mainly directed at assuring the patient of his safety. This is accomplished by helping the patient manage his or her thoughts and responses in order to feel as comfortable as possible. The voice-over explains to the patient where he or she is and provides certain information as to what is happening in the intraoperative period of the surgery. The voice-over also contains suggestions and guided imagery, now familiar to the patient as they repeat and reinforce the information, reassurance and suggestions given on the preoperative tape. A representative intraoperative tape of the present invention, © 1991 P.I.P. Surgical Audiotape Series, Inc., contains a voice-over portion as follows:

MUSIC ALONE

I. The music that you are hearing now is the same music that you have been listening to right along . . . the same music that you heard before your surgery . . . The main difference is that now you are in the operating room. Your doctors have put you to sleep, and your surgery has started. You are safe.

You are in safe hands. And you can leave the work of surgery to your doctors. They have performed this operation many, many times... and they know exactly what to do.

II. Your anesthesiologist knows exactly how to care for you... and all the other people in the operating room know what to do, and when to do it. Everyone is working together to care for you... and so you can relax... you can relax now... and let them do what they do best.

III. And while they work, I want you to continue listening to me... and I want you to continue listening to the music. Just as I said before, the music will continue to play throughout your surgery. All you need to do is listen... and remember that the music is there to help you feel more comfortable and more relaxed. Just as you did before your surgery started, listen to the music again... listen... and let the music bathe you in a warm bath of sound... let the music calm and comfort you... let the music play for you... relaxing... and soothing... and comforting you...

MUSIC ALONE

IV. And while you listen to the music, tell your body to rest and relax... Tell your body to let go of the tension everywhere... Remember that you are safe... and so it is safe for you to relax... You are safe... and so you can tell your whole body to rest and relax.

MUSIC ALONE

V. Listen to the music... and feel calm and comforted... now beginning to feel relaxed, and letting yourself drift with the music... drifting smoothly, gently back to your island... to your island far, far away... back to the beach where the sand is clean and white and velvety soft... Float gently down to the warm sand on the beach... and rest... feel the sun warming your body... and rest... smelling the salt air... and hearing the waves as they roll up and over, and over and over again... washing and smoothing the sand...

MUSIC ALONE

VI. Listen to the music... and rest... drifting and floating with the music... now drifting back to the place that is all your own... your safe place... your peaceful, quiet place... the place that is all your own where you love to be... seeing all the things that you know and love to see... hearing all the sounds that you love to hear... drifting and listening... drifting and noticing all the things around you that you love... drifting and resting... feeling very, very comfortable... and very, very relaxed...

MUSIC ALONE

VII. Listen to the music... for now, all you need do is listen to the music... soothing and comforting... relaxing... and peaceful...

MUSIC ALONE

VIII. And when you wake up, I will be talking to you once again... and you will hear the music playing again... and feel comforted... and relaxed... and safe. For now, listen to the music... Let the music bathe you in a warm bath of sound... Let the music wash over you... warming and comforting... Drift with the music... feeling calm... and comfortable... and very, very relaxed.

MUSIC ALONE

And now...

The tape is recorded on both sides. Side one plays from the beginning to the end of section VIII. It then repeats sections I through VIII two more times for a total of three times. Side 2 of the tape is the same as side 1; and the tape automatically reverses to the second side of the tape.

For the third postoperative period of the surgery, a third tape is provided. The music on this tape is the same music as the music on the first two tapes. The opening and closing themes are identical to the other two tapes so as to provide a continuing familiarity for the patient, and a starting of the music where the music on the intraoperative tape left off.

Since a primary purpose of the three tapes and the procedure of the present invention is to shorten the recovery time of the patient, the information contained on the postoperative tape is more detailed with respect to what the patient encounters in the recovery room after the surgical procedure. The purpose of this information is to provide continuity and to allay any fears, anxiety and discomfort the patient may experience due to the strange surroundings and busy, impersonal atmosphere normally encountered in the recovery room.

A presently preferred postoperative tape, © 1991 P.I.P., Surgical Audiotape Series, Inc., includes the following voice-over portion:

I. The music that you are hearing is the same music that you have heard before... Now the only difference is that your surgery is finished. Your surgery is over... and you are beginning your recovery. In the recovery room there are many special people who know what you need, and how to care for you. They are specialists in helping people as they wake up from the anesthesia and begin to recover. Let them help you. Let them take care of you, and as they care for you, let yourself drift and listen to the music... As you begin to drift awake, continue to listen to the music... Let the music soothe and comfort you just as it has before... drift... and float gently back to sleep with the music...

MUSIC ALONE

II. As you start your recovery, there will be many interruptions. The nurses will need to stop the tape to ask you a question, or to tell you something. They may check your blood pressure, or your bandage... You will feel them caring for you, and know that all the things they do are part of helping you begin your recovery from surgery. And while they care for you, don't be surprised if you hear a lot of loud noise in the recovery room. It is a busy, noisy place, and when you first wake up from the anesthesia, everything may sound very, very loud... If this happens, don't let it bother you... as soon as the nurses finish talking to you, you may return to the tape and continue listening... Just continue to listen... listen and rest... relax and drift... Tune out all the noise that you hear in the recovery room... and tune in to the music on the tape... Listen to the music... and rest... relax and drift... floating gently back to sleep with the music.

MUSIC ALONE

III. . . . And now as you begin to wake up, you will be aware of many different things . . . feeling sleepy and drowsy . . . and at first it may be very hard to think . . . It's okay to feel this way. It's natural to feel this way when you first wake up from surgery. Most people feel very sleepy, and for now, the best thing you can do is relax . . . relax . . . and let yourself drift in and out of sleep . . . When you open your eyes, the lights will seem very, very bright . . . and it will be hard to see . . . everything may seem very blurry at first . . . That's okay, too. It's another part of waking up from the anesthesia. For now, it's o.k. to keep your eyes closed because in a little while it will be easier for you to see. For now, relax . . . let your eyes remain closed, and let yourself drift with the music . . .

MUSIC ALONE

IV. . . . And now you may be aware of other new feelings . . . Your throat may feel sore. That's because there was a tube that breathed for you during your surgery. Now that you are awake, it's natural for your throat to feel sore, but you don't have to let it bother you. You know why your throat feels sore, but you can expect the soreness to go away soon . . . And now there is also something that you can do to help your throat feel better . . . Try to imagine holding a glass of something cool that you like to drink . . . Think about something that you really like . . . something so cold and soothing that when you swallow it, you can imagine the soreness going away . . . Imagine the coolness now . . . imagine swallowing the cool liquid and letting the coolness stay in your throat . . . Now feel the cool, cold liquid soothing your throat . . . and now feel the soreness beginning to go . . . Let your throat relax . . . and as your throat begins to relax, let yourself continue to drift and listen to the music . . . relax . . . and drift . . . listening to the music . . . resting and relaxing . . . The more you relax, the more comfortable you will feel.

MUSIC ALONE

V. . . . And now you may be aware of the bandages covering your surgery . . . and the soreness underneath and around that part of your body. It's natural to feel sore and uncomfortable after surgery . . . Tell yourself not to let it bother you . . . Remind yourself that it won't last . . . And Remember that when you start to relax, you will start to feel more comfortable. Tell your body to relax . . . tell the muscles all around your surgery to loosen up and to let go . . . and let the sound of the music help you to relax . . . Tune in to the music, and let the music bathe you in a warm bath of sound . . . soothing and relaxing your muscles. And now feel the muscles all around your surgery begin to grow soft . . . and feel the muscles underneath your incision becoming loose and relaxed . . . Imagine the softness in these muscles spreading slowly throughout your whole body . . . relaxing and soothing . . . allowing all the muscles in your body to release and relax . . . And know that whenever you like, whenever you wish to tune in to the music, you can let the sound of the music wash over you . . . You can feel the music relaxing your body . . . You can even feel all the muscles in your whole body growing more and more soft . . . more and more relaxed . . . and even more and more comfortable . . . For now, just drift and float with the music . . . rest . . . and listen to the music . . .

MUSIC ALONE

VI. . . . And now you may be aware of other tubes . . . They are all there to help your body recover from surgery. In the beginning, there are tubes to help drain and remove fluid and swelling from around the place where you had surgery . . . other tubes are there to make it easier to give you medicine that will also help you to recover . . . all of the tubes are there to help you recover from surgery . . . and to help your body begin the healing process. The tubes are there to do the work for you . . . and you can help the most by relaxing and letting them do their work . . . Tell yourself that if the tubes feel uncomfortable, it won't last long . . . Tell yourself not to let them bother you because they are there to make you well . . . Remind yourself that the parts of your body that feel sore and tight will feel better soon . . . And tell the sore parts to relax. Tell the sore muscles to let go . . . to begin to feel loose and soft . . . And let yourself drift and drowse again . . . and listen to the music . . . knowing that each time you hear the music, it will be a signal to relax even more . . . to float with the music . . . beginning to know that the more you relax, the more comfortable you will feel.

MUSIC ALONE

VII. . . . And now as you begin to wake up even more, you may want something. At first it may be difficult to speak . . . it's almost always hard to talk when you first wake up from the anesthesia. The nurses caring for you know that it's hard to speak . . . They are very good at guessing what you may want because they have taken care of so many other patients who are like you . . . So, if you need something, try to tell someone what you want. Ask someone to help you. If at first it's difficult, don't let it bother you . . . don't let it stop you from trying again a little later . . . and remind yourself that it won't last long, and that you will be able to speak clearly soon.

VIII. And remember that from time to time there will be interruptions as the nurses stop the tape to ask you a question or to tell you something. And when they are finished talking to you, you may return to the tape and continue listening . . . listening to the music . . . and drifting gently back to sleep.

MUSIC ALONE

IX. . . . And now while you listen to the music, the nurses will continue caring for you. They may empty the drains, or put medicine in a tube . . . or take your temperature. Don't let any of these interruptions bother you . . . they are all part of helping you recover from your surgery. All you have to do is let the nurses care for you while you rest and allow the music to wash over you, relaxing and soothing. tune out the interruptions . . . and tune out the bright lights in the recovery room . . . Tune out anything else that may bother you . . . and tune in to the music. Let the music play for you and comfort you . . . For now, the best thing that you can do is relax, and let the people caring for you do what they do best . . . let the tubes and the medicine work for you . . . while you take charge of relaxing your body. The more you relax, the more comfortable you will feel.

MUSIC ALONE

X. For now, don't try to think. Push the thoughts away . . . and know that you can return to them later whenever you feel like it . . . For now, the best thing that you can do is relax . . . Later, if something worries you, you will be able to talk to someone about it. You will be able to talk to someone who can help you. Later, when you are feeling more awake, and feeling better, there will be time to ask questions . . . and there will always be someone who can help you. For now, there is nothing that you have to do except listen to the music. Listen to the music, and let the music bathe you in a warm bath of sound . . . soothing . . . relaxing . . . comforting . . .

MUSIC ALONE

XI. And while you listen, let the music help you drift . . . drift and return to your favorite place . . . the safe place that you found before, where you can feel comfortable and calm . . . where you know that you can go to feel very, very relaxed . . . and very, very peaceful . . . Take yourself there now . . . let yourself drift back to your place, and begin to imagine how it looks. Look around you, and notice that you see . . . Look at the colors . . . Notice the smells . . . Listen to the sounds that you hear all around you . . . and listen to the music floating in and all around you . . .

MUSIC ALONE

. . . And now find the special place that was so comfortable before . . . see yourself sitting down . . . or stretching out to rest more comfortably . . . and look at all the things that you enjoy and love to see . . . enjoying everything that you do . . . and everything that you see . . . feeling safe in this special place . . . resting and relaxing . . . feeling very peaceful . . . and very, very comfortable . . . drifting . . . and listening to the music . . .

MUSIC ALONE

XII. Drifting . . . and now . . . perhaps returning to your favorite island . . . to the beach on your island where the soft sand stretches for miles and miles, as far as you can see . . . Take yourself there and feel the warm sand on the beach . . . Lie down on the sand and feel its warmth . . . Feel the sun warming your body, and feel your whole body relaxing as you are gently warmed by the sun . . . and gently held and comforted by the warmth and the sand beneath you . . . Hear the sound of the waves rolling over and over, washing and smoothing the sand, over and over again . . . Smell the salt air, and feel the gentle breeze . . . Hear a seabird calling somewhere . . . and see the sky overhead, blue and clear . . . and the sea below, deep blue with white caps rising and falling . . . And now, if you like, imagine yourself resting under the shade of a tree . . . resting on the soft sand, feeling cool and comfortable . . . looking out at the water . . . From your cool place under the tree, you can still see the waves rolling gently toward the beach . . . and the blue, blue sky . . . You can hear the sound of a seabird calling . . . and the soft rustling of the palm leaves in the breeze . . . Wherever you are, in your real or in your imaginary place, let yourself be completely comfortable and at peace . . . Let yourself rest . . . and feel your whole body growing heavy with relaxation . . . becoming more and more comfortable, and more and more relaxed.

MUSIC ALONE

XIII. Let yourself stay for as long as you like . . . resting and growing even more relaxed . . . knowing that you can return any time that you wish . . . knowing that your special place will always be here for you whenever you wish . . . wherever it may be. And so you may continue to drift . . . and relax . . . and rest . . . listening to the music . . . and letting the sound of the music move gently all around you . . . calming and comforting and soothing . . . bathed in the warm bath of sound . . . feeling very, very relaxed . . . drifting . . . and listening to the music . . .

MUSIC ALONE

XIV. And as you continue to listen, the tape will return to the beginning. You may continue to listen as often as you like. When you don't feel like listening any more, you may take off the earphones . . . or you may drift off to sleep . . . waking and listening . . . drifting and sleeping . . . listening . . . and letting yourself grow more and more relaxed . . . more and more comfortable. The more you relax, the more comfortable you feel. The more comfortable you feel, the more rapidly you will recover from surgery.

XV. So . . . drift now . . . listening to the music . . . resting and relaxing . . . feeling very calm and very peaceful . . . comfortable . . . feeling very, very comfortable . . . and very, very relaxed . . .

MUSIC ALONE

Side 1 of the postoperative tape contains, in its entirety, segments I through XV. Side 2 is the same as side 1 and the tape player reverses automatically to side 2.

All three tape cartridges are color coded with black for the preoperative cartridge, red for the intraoperative cartridge and blue for the postoperative cartridge for the purpose of avoiding mistakes in giving patients the wrong tape at the wrong moment. The tape playback equipment is selected for ease in use and durability. Although a tape cassette and recording system is presently preferred, it is understood that other recording and playback systems may be used as, for example, a compact or mini disk system.

The particular content of the tapes as described above has been made for patients who will undergo general anesthesia. The content of the voice-over information and suggestions to the patient will be the same for all surgical procedures with which the patient uses the present system. However, the content is different when the patient is conscious during the intraoperative phase of the surgery. In such cases, the patient may only be lightly sedated or receive local or regional anesthesia. In all cases, however, the type and repetitiveness of the music on the tapes are as described above. Also, the voice-over information for each tape is directed to the circumstances of the particular period of the surgery for which the tape is used.

Where the system of the present invention is used with patients receiving light sedation or undergoing only a regional or local anesthesia and where the patient will be conscious during the surgical procedure, a single tape is provided for the preoperative period and a second tape combines the intraoperative and postoperative periods. The voice-over content is similar to that of the three separate tapes that are written for patients to hear under general anesthesia. However, the messages avoid reference to the procedures used only in general anesthesia and acknowledge instead that the patient will be awake and aware of activity in the operating room. The music is identical to the music composed for the general anesthesia tapes.

In all cases, the voice over on the tape is recorded in a deliberate, slow pace, with careful attention to balance between the music and voice; at all times the voice is soft in order to soothe the patient, and the pace deliberately slow to allow the patient ample time to understand and assimilate the meaning of the information, reassurance and suggestions while the patient experiences the altered effect of anesthesia or sedation.

A representative preoperative tape for the two tape series where the patient remains conscious during the surgical procedure, © 1992 P.I.P. Surgical Audiotape Series, Inc., contains a voice-over portion as follows:

PREOPERATIVE

I. The tape that you are listening to was made for patients to hear before they have surgery. We know that this is an especially difficult time for everyone . . . this waiting time when it's often what we don't know that makes us feel even more scared. And so this first tape was made in order to help you feel as comfortable as you can while you wait. We know that the more relaxed and comfortable you are, the more easily you will manage your surgery . . . and the more rapidly you will recover.

II. A little later, since you'll be awake in the operating room, you'll be able to listen to a second tape that was made especially for you to hear while you're having surgery . . . and you'll be able to continue listening to this tape after your surgery is finished, and as you begin your recovery. It's also O.K. to stop the tape when you don't feel like listening any more . . . and know that you can always continue to listen again whenever you feel like it . . .

III. For now, just begin by listening to the tape. The tape will play and repeat, and you may hear it as often as you like. Our goal is to give you the kind of information and suggestions that will help you manage each part of your surgery as comfortably as possible. And our goal is also to help you take charge of yourself and what happens to you. The trick is in knowing that there is something that you can do . . . There are ways to feel more comfortable and relaxed . . . simple things that you can do for yourself.

IV. And you can start right now! You can begin no matter where you are . . . Whether you are sitting up, or lying down, you can relax anywhere at any time. Whether you are in the operating room or beginning your recovery from surgery, the best thing you can always do is close your eyes, and close out everything around you. So begin now by closing your eyes . . . Close out the hospital . . . Close out everything all around you, and start to listen even more carefully to the messages on the tape. For now, don't try to think. Push away the thoughts . . . and know that you can return to them later whenever you feel like it. Later, if something bothers you, you'll be able to talk to someone who can help you . . . For now, with your eyes closed, and your eyelids beginning to feel heavy over your eyes, you are beginning to take charge of relaxing your body.

V. Nobody knows exactly how it works, but we do know that when you simply think about wanting your body to relax, somehow you can make it happen . . . And so, with your eyes still closed, begin by thinking about your right hand. Make it into a fist . . . and now make it tight . . . squeeze your fist . . . Tight Even tighter! And now, let it go . . . let your fingers go . . . Let your fingers relax, and let your hand rest gently . . . Let your whole hand relax and rest . . .

VI. And now try the same thing with your left hand. Make a fist . . . Make it tight! Even tighter! Hold it tight! And now, let it go . . . Let your fingers relax . . . and let your whole hand rest gently.

VII. Now, if you feel like it, you can move on, and do the same thing with the rest of your body . . . Start by thinking about a part of your body that feels really tense. Feel the tension . . . Think about the tension . . . And now tell that part of your body to relax and let go . . . Just as you told your fingers and your hand to relax, tell that part of your body to let go and rest . . . The more you tell your body to relax, the easier you will find it to relax . . . and the more you will begin to notice that you are beginning to relax . . . So rest now . . . Tell your whole body to rest and relax . . . tell the muscles that feel so tight and tense to relax . . . and now imagine those muscles beginning to grow soft and heavy . . . and very, very relaxed . . .

VIII. Let the softness spread to other parts of your body . . . Let it begin to flow from the top of your head . . . and then . . . bit by bit, all the way down to your feet . . . and on down to the tips of your toes . . . Rest . . . and let your whole body grow even more deeply relaxed and comfortable.

IX. And as you rest, begin to notice the music that has been playing in the background while I've been talking to you . . . Begin to tune in to the music, and for now, tune out anything that bothers you.

MUSIC ALONE

X. You don't have to think about anything else . . . Just let the music bathe you in a warm bath of sound . . . Let the music wash over your whole body . . . relaxing and soothing you . . . helping your whole body relax . . . allowing your muscles to relax and let go their tension . . . of letting your mind begin to drift peacefully . . . letting your mind and your body rest and relax to the sound of the music . . . Listen . . . Listen to the music . . .

MUSIC ALONE

XI. Listen to the music . . . knowing that the music is there to help you feel more comfortable and more relaxed . . . knowing that each time you hear the music, it will be a signal to relax even more . . . Drift with the music . . . and let the sound of the music move gently all around you . . . calming and comforting and soothing . . .

MUSIC ALONE

XII. Tell your whole body to rest and relax . . . and let your body grow even more deeply relaxed . . . let go the tension in your whole body . . . and feel so very, very relaxed . . . comfortable . . . calm . . . and very, very relaxed . . .

XIII. And now . . . with your eyes still closed, feeling very, very relaxed . . . listening to the music and feeling completely relaxed and peaceful . . . I want you to take yourself off to another place . . . far, far away . . . A place that I will tell you about . . . a place, somewhere, where you can imagine yourself being . . . where you can take yourself now . . . and imagine that you are there . . .

XIV. Let it be an island, somewhere far, far away . . . with a beach . . . and miles and miles of clean, white, velvety soft sand . . . Take yourself there now, and feel the warm sand on the beach . . . Lie down on the sand and feel its warmth . . . feel the soft sand holding your body, and the sun warming your body as you rest on the beach . . . Feel your whole body relaxing as you are gently warmed by the sun . . . And now feel the breeze touching your skin, and hear the leaves of the palm trees brushing softly against each other . . . Hear the waves rolling up over the sand . . . each wave followed by another . . . rolling over and over, again and again, washing and smoothing the sand . . . Smell the salt air . . . and now hear a seabird calling somewhere in the distance . . . And now, if you like, imagine yourself resting under the shade of a tree . . . resting on the soft, clean sand, feeling cool and comfortable . . . looking out at the water . . . From your cool place under the tree, you can still see the waves rolling back slowly toward the beach . . . and the clear, blue sky overhead . . . the sea below, deep blue, with white caps rising and falling . . .

XV. And as you lie on the beach, relaxed and very, very comfortable, let this be your Special Place . . . Stay here as long as you like . . . resting and relaxing . . . knowing that when you leave, you may return any time that you wish . . . knowing that your Special Place will always be waiting for you . . . peaceful and safe . . . a place where you can always come and go whenever you wish . . . where you will always feel comfortable and calm . . . peaceful and very safe . . . restful . . . and very, very relaxed . . .

MUSIC ALONE

XVI. And now . . . with your eyes still closed, drifting and floating with the music, feeling very, very relaxed and peaceful, let yourself travel to another place . . . Perhaps this place will be one that you already know . . . a place that you remember well because you have always loved being there, and you know that you will enjoy being there again . . . Let this place be as peaceful as your island . . . Let it be a quiet, restful place where you will also feel comfortable and safe.

XVII. Take yourself there now, and begin to imagine how it will look when you arrive . . . What will you see when you get there? . . . Imagine yourself there now . . . and find a spot that looks comfortable . . . See yourself sitting down, or perhaps you'd rather lie down and stretch out to feel completely comfortable . . . And when you have found your comfortable spot, look around, and begin to notice all the things that you see . . . Imagine seeing things that you know and love . . . and let yourself look closely at each object . . . Look at the shape of each thing around you, and notice whether it is big, or small . . . Perhaps there is something that you want to hold or touch . . . Maybe it is soft . . . Notice its color . . . is it pale? Or is it bright? Listen to the sounds that you hear all around you . . . and smell the scent of something that pleases you . . . the scent of something that you remember enjoying when you were here before . . . And now as you look around, take pleasure and comfort in being here . . . Feel yourself relaxing and enjoying your place . . . feel safe . . . and very peaceful . . . and very, very relaxed . . . Let yourself stay here for as long as you like . . . resting and growing even more relaxed . . . knowing that you may return any time that you wish . . . knowing that your special place will always be here for you whenever you wish to return . . .

MUSIC ALONE

XVIII. Wherever it is that you imagine yourself to be, let it be a place that is always safe and comfortable . . . where you can listen to the music as you relax in your Special Place . . . where you can drift with the music . . . floating in and out of sleep . . . floating . . . resting . . . relaxed and comfortable . . . very peaceful . . . and very, very relaxed . . .

MUSIC ALONE (tape returns to X., and plays through to the end; automatic reverses to side 2, where it starts at the beginning, identical to side 1).

The combined intraoperative and postoperative tape for the two tape series, © 1992 P.I.P. Surgical Audiotape Series, Inc., contains a voice-over portion as follows:

MUSIC ALONE

I. And now . . . with your eyes closed, continue to listen to the music . . . Just as you did before your surgery started, listen to the music again . . . Listen . . . and let the music bathe you in a warm bath of sound . . . Close out everything all around you, and let the music calm and comfort you . . . Let the music play for you, knowing that each time you hear the music, it will be a signal to relax even more . . .

II. Knowing that from now on you can relax and rest, and leave the work of surgery to your doctors. they have performed this operation many, many times . . . And they know exactly what to do . . .

III. Your anesthesiologist knows exactly how to care for you . . . and all the other people in the operating room know what to do, and when to do it. Everyone is working together to care for you . . . and so you can relax . . . you can relax now . . . and let them do what they do best.

IV. And while they work, continue listening to me . . . and to the music . . . and as you listen, remind your body to rest and relax . . . Tell your body to let go of the tension everywhere . . . remember that you are safe . . . you are in safe hands . . . and so it is safe for you to relax . . . you are safe . . . and so you can tell your whole body to rest and relax . . .

V. From time to time, there will be interruptions as someone needs to stop the tape to tell you something, or ask you a question. When they are finished talking to you, you may return to the tape, and continue listening . . . Listen . . . and let the music soothe and comfort you, just as it has before . . . Drift . . . and float gently to sleep with the music . . . Drift . . . and Rest . . . tuning in to the music . . . feeling your body growing even more deeply relaxed and comfortable . . . letting your mind and your body rest and relax to the sound of the music . . .

MUSIC ALONE

VI. Float with the music . . . and drift gently back to your island . . . to your island far, far away . . . back to the beach, where the sand is clean, and white, and velvety soft . . . Float gently down to the warm sand on the beach . . . and rest . . . Feel the sun warming your body . . . and rest . . . smelling the salt air . . . and hearing the waves rolling smoothly, evenly, up and over the sand . . . rolling over and over again . . . washing and smoothing the sand . . . And as you lie on the beach, feeling relaxed and very, very comfortable, know that you may stay here as long as you like . . . resting . . . relaxing . . . knowing that when you decide to leave, you may return any time that you wish . . . knowing that your Special Place will always be waiting for you . . . peaceful and safe . . . a place that will always be here for you whenever you want . . . comforting . . . safe . . . restful . . . .

MUSIC ALONE

VII. And as you drift, listening to the music, remember that from time to time there will be interruptions . . . but you don't have to let them bother you . . . Someone may stop the tape to talk to you, or ask you to do something . . . and after your surgery is finished, you will feel the nurses caring for you . . . checking your blood pressure, or your bandage . . . and you will know that all the things they do are part of helping you begin your recovery from surgery . . .

VIII. And as you start to recover, you may be aware of the soreness underneath and around the bandages covering your surgery. It's natural to feel sore and uncomfortable after surgery . . . Tell yourself not to let it bother you . . . and remind yourself that it won't last . . . Tell yourself not to let it bother you . . . Remember that when you start to relax, you will start to feel more comfortable. And just as you told your body to relax before surgery, tell your body to relax now . . . Tell the muscles all around your surgery to loosen up, and to let go . . . And let the sound of the music help you relax . . . Tune in to the music, and let the music bathe you in a warm bath of sound . . . soothing and relaxing all your muscles . . . And now feel the muscles all around your surgery begin to grow soft . . . and feel the muscles underneath your incision becoming loose and relaxed . . . Imagine the softness in these muscles spreading slowly throughout your whole body . . . relaxing and soothing . . . allowing all the muscles in your body to release and relax . . .

IX. And know that whenever you like, whenever you wish to tune in to the music, you can let the sound of the music wash over you . . . You can feel the music relaxing your body . . . You can even feel all the muscles in your whole body growing more and more soft . . . more and more relaxed . . . and even more and more comfortable . . . For now, just drift, and float with the music . . . Rest . . . and listen to the music . . .

MUSIC ALONE

X. As you continue to recover from surgery, you may be aware of different tubes that are attached to your body . . . they are there to help your body begin the healing process . . . There may be tubes to help drain and remove fluid and swelling from around the place where you had surgery . . . other tubes are there to make it easier to give you medicine that will also help you to recover . . . All of the tubes are there to help you recover from surgery . . . and to help your body heal itself. The tubes are there to do the work for you . . . and you can help the most by relaxing, and letting them do their work . . . Tell yourself not to let them bother you because they are there to make you well . . . Remind yourself that the parts of your body that feel sore and tight will feel better soon . . . And tell the sore parts to relax. Tell the sore muscles to let go . . . to begin to feel loose and soft . . .

XI. And let yourself drift and drowse again . . . Listen to the music . . . knowing that each time you hear the music, it will be a signal to relax even more . . . to float with the music . . . beginning to know that the more you relax, the more comfortable you will feel.

MUSIC ALONE

XII. And now remind yourself that if you're feeling uncomfortable, it won't last long . . . Remind your body to relax, and tell your muscles to let go their tension . . . Tune in to the music, allowing the music to wash over you, relaxing and soothing . . . Letting the music play for you, and comfort you . . . Letting the people caring for you to do what they do best . . . Letting the tubes and the medicine work for you . . . while you take charge of relaxing your body . . . knowing that the more you relax, the more comfortable you will feel.

MUSIC ALONE

XIII. For now, don't try to think. Push away the thoughts . . . and know that you can return to them later whenever you feel like it . . . For now, the best thing you can do is relax. For now, there is nothing that you need to do except listen to the music. Listen to the music, and let the music bathe you in a warm bath of soothing sound . . . relaxing . . . calming . . . comforting . . .

MUSIC ALONE

XIV. Listen to the music . . . and feel calm and comforted . . . Listen to the music . . . and let yourself drift and float. Listen to the music . . . and let the sound of the music move gently all around you, knowing that the more you relax, the more comfortable you will feel.

XV. And with your eyes still closed, feeling very, very relaxed . . . drifting and listening to the music, let yourself float gently to another place . . . perhaps floating back this time to another island . . . and a different beach . . . Perhaps it will be a beach that you already know . . . or if you prefer, let yourself imagine an imaginary beach . . . And now see yourself there, resting and relaxing . . . Imagine looking at something new . . . something that you have always wanted to see . . . and take yourself there to enjoy whatever it is that you want to see . . . Wherever you are, relaxed and very, very comfortable, let this be another Special Place . . . and know that you are free to travel to as many different places as you like . . . Let each Place be peaceful and safe . . . restful and relaxing . . . Where you can stay for as long as you like . . . and return whenever you wish . . .

MUSIC ALONE

XVI. And now, if you feel like it, with your eyes still closed, drifting and floating with the music, let yourself drift back to your other very Special Place . . . the one that only you know about, where you returned before because you loved being there . . . and you know that you will enjoy being there again . . . Imagine yourself there . . . feeling so safe and peaceful . . . feeling completely comfortable . . . and taking pleasure in looking closely at all the things you love to see . . . noticing the shape of each object . . . feeling something that is soft and pleasant to hold . . . looking at the different colors, and listening to the sounds that you hear all around you . . . smelling the scent of something that makes you feel especially content and comfortable . . . feeling very safe and peaceful . . . calm . . . comfortable . . . and very, very relaxed . . . And let yourself stay here in this very Special Place for as long as you like . . . Resting and growing even more relaxed . . . knowing that you may return any time that you wish . . . knowing that this Special Place will always be here for you whenever you wish to return . . . Knowing that wherever you are, wherever you may be, you can return to your favorite place . . . You can listen to the music . . . and tell your body to rest and relax . . . You can relax anywhere at any time . . . knowing now that the more you relax, the more comfortable you will feel . . . and the more comfortable you feel, the more you will be able to relax . . .

MUSIC ALONE

XVII. Drift now . . . Listening to the music . . . Resting and relaxing . . . Letting the sound of the music move gently all around you . . . Bathed in the warm bath of sound . . . floating . . . Feeling very calm, and very peaceful . . . Comfortable . . . Feeling very, very comfortable . . . Resting . . . Listening to the music . . . Resting . . . And feeling very, very relaxed . . .

MUSIC ALONE

The preoperative tape is played without interruption for the duration of the preoperative period, automatically reversing and repeating as often as necessary. It is preferable that the combined intraoperative and postoperative tape start to play before the patient is given sedation or local or regional anesthesia and that it continue to play uninterruptedly for the duration of the surgery and the patient's stay in the recovery room.

I claim:

1. A method of relaxing surgical patients and for reducing tension, anxiety and stress associated with the perioperative period of surgery, said perioperative period beginning with a preoperative period, continuing through an intraoperative period and concluding at the end of a postoperative period, which method comprises the steps of:
    a) providing a first combination of music and voice to the surgical patient in the first preoperative period of the surgery before a surgical procedure commences;
    b) providing at least one further combination of music and voice in the second intraoperative and third postoperative period of the surgery while the surgical procedure is being performed and immediately after the surgical procedure while the patient is in a postoperative recovery room;
    c) the music of each combination is anxiolytic, without extremes in rhythm, melody or dynamics and without familiarity or memory association and is composed to give a pattern of sound which in turn gives an impression to the patient of an enveloping, soothing, cohesive structure of notes for relaxing the patient and reducing tension, anxiety, stress and discomfort associated with the perioperative period of the surgery; and
    d) the voice of each combination is provided at the same time as the music to give general information common to the perioperative period and repetitious suggestions to the patient on how to relax and reduce tension, anxiety, stress and discomfort associated with the perioperative period.

2. A method of relaxing surgical patients and for reducing tension, anxiety and stress associated with the perioperative period of surgery, said perioperative period beginning with a preoperative period, continuing through an intraoperative period and concluding at the end of a postoperative period, which method comprises the steps of:
    a) providing a first combination of music and voice to the surgical patient in the first preoperative period of the surgery before a surgical procedure commences;
    b) providing a second combination of music and voice in the second intraoperative period of the surgery while the surgical procedure is being performed under local or regional anesthesia and in the third postoperative period immediately after the surgical procedure while the patient is in a postoperative recovery room;
    c) the music of each combination is anxiolytic, without extremes in rhythm, melody or dynamics and without familiarity or memory association and is composed to give a pattern of sound which in turn gives an impression to the patient of an enveloping, soothing, cohesive structure of notes for relaxing the patient and reducing tension, anxiety, stress and discomfort associated with the perioperative period of the surgery; and
    d) the voice of each combination is provided at the same time as the music so as to give general information common to the perioperative period and repetitious suggestions to the patient on how to relax and reduce tension, anxiety, stress, discomfort associated with the perioperative period.

3. The method according to claim 2 wherein:

a) the information given in the first combination relates to the preoperative period of the surgery and acknowledges some of the most common preoperative conditions the patient may be experiencing; and b) the information given in the second combination relates to the intraoperative period and postoperative period of the surgery and explains the intraoperative and postoperative conditions the patient may be experiencing.

4. The method according to claim 3 wherein:

a) the music of the first combination is played continuously while the patient is experiencing the conditions of the preoperative period to provide an unbroken flow of soothing sound; and b) the music of the second combination is played continuously while the patient is experiencing the conditions of the intraoperative and postoperative periods.

5. The method according to claim 4 wherein the music in each combination is played at varying intervals without voice to give the patient time to relax still further or to create a personal visualization in order to enhance the patient's relaxing.

6. The method according to claim 5 wherein the first combination of music and voice is provided to the patient about 30–45 minutes before the second intraoperative period of the surgery.

7. The method according to claim 5 wherein:

a) the music of each combination consists of an opening theme, a middle section and a closing theme; and b) the opening and closing themes of the music of each combination for each of the three periods of surgery is the same.

8. The method according to claim 7 wherein:

a) the middle section of the music of each combination is the same.

9. The method according to claim 7 wherein the information given in the first combination further informs the patient to expect one more tape during the surgical procedure and after the surgical procedure.

10. The method according to claim 8 wherein the music and voice of each combination is provided to the patient while blocking out other sounds.

11. The method according to claim 10 wherein the music and voice of each combination is provided on separate tape recordings and is provided to the patient through earphones.

12. The method according to claim 5 wherein the music portion of each combination is provided substantially in major keys.

13. The method according to claim 11 wherein:

a) the music and voice of each combination is provided on separate tapes with both sides of a single tape being identical; and b) the tapes are played first on one side and then on the other and repeatedly again on the one side and the other as long as the patient is experiencing the conditions of the particular perioperative period for which the tape is applicable.

14. The method according to claim 13 wherein:

a) the tape is played in a tape playback machine to play automatically and repeatedly first one side and then the other side of the tape in order to give the patient continuous music and voice during the particular perioperative period for which the tape is applicable.

15. A method of relaxing surgical patients and for reducing tension, anxiety and stress associated with the perioperative period of surgery, said perioperative period beginning with a preoperative period, continuing through an intraoperative period and concluding at the end of a postoperative period, which comprises the steps of:

a) providing a first combination of music and voice to the surgical patient in the first preoperative period of the surgery before a surgical procedure commences;

b) providing a second combination of music and voice in the second intraoperative period of the surgery while the surgical procedure is being performed under general anesthesia;

c) providing a third combination of music and voice in the third postoperative period of the surgery immediately after the surgical procedure and while the patient is in a postoperative recovery room;

d) the music of each combination is anxiolytic, without extremes in rhythm, melody or dynamics and without familiarity or memory association and is composed to give a pattern of sound which in turn gives an impression to the patient of an enveloping, soothing, cohesive structure of notes for relaxing the patient and reducing tension, anxiety, stress and discomfort associated with the perioperative period of the surgery; and e) the voice of each combination is provided at the same time as the music so as to give general information common to the perioperative period and repetitious suggestions to the patient on how to relax and reduce tension, anxiety, stress and discomfort associated with the perioperative period.

16. The method according to claim 15 wherein the music of each combination is played continuously to provide an unbroken flow of soothing sound.

17. The method according to claim 16 wherein the music in each combination is played at varying intervals without voice to give the patient time to relax still further or to create a personal visualization in order to enhance the patient's relaxing.

18. The method according to claim 17 wherein the first combination of music and voice is provided to the patient about 30–45 minutes before the second intraoperative period of the surgery.

19. The method according to claim 18 wherein:

a) the music of each combination consists of an opening theme, a middle section and a closing theme; and b) the opening and closing themes of the music of each combination for each of the three periods of surgery is the same.

20. The method according to claim 18 wherein:

a) the middle section of the music of each combination is the same.

21. The method according to any one of claims 15–18 and 19–20 wherein:

a) the information given in the first combination relates to the preoperative period of the surgery and acknowledges some of the most common preoperative conditions the patient may be experiencing;

b) the information given in the second combination relates to the intraoperative period of the surgery and explains the intraoperative conditions the patient may be experiencing; and c) the information given in the third combination relates to the postoperative period of the surgery and explains the postoperative conditions the patient may be experiencing.

22. The method according to claim 21 wherein the information given in the first combination further informs the patient to expect two more tapes, the second during the surgical procedure and the third after the surgical procedure.

23. The method according to claim 20 wherein the music and voice of each combination is provided to the patient while blocking out other sounds.

24. The method according to claim 21 wherein the music and voice of each combination is provided on separate tape recordings and is provided to the patient through earphones.

25. The method according to claim 22 wherein:
a) the music and voice of each combination is provided on separate tapes with both sides of a single tape being identical, and
b) the tapes are played first on one side and then on the other and repeatedly again on the one side and the other as long as the patient is experiencing the conditions of the particular perioperative period for which the tape is applicable.

26. The method according to claim 25 wherein:
a) the tape is played in a tape playback machine to automatically repeatedly play first one side and then the other side of the tape in order to continuously give the patient said music and voice during the particular perioperative period for which the tape is applicable.

27. The method according to claim 23 wherein the music portion of each combination is provided substantially in major keys.

* * * * *